United States Patent
Kim et al.

(10) Patent No.: US 10,786,180 B2
(45) Date of Patent: Sep. 29, 2020

(54) INTRAFRACTIONAL MOTION REDUCTION SYSTEM USING AUDIOVISUAL-AIDED INTERACTIVE GUIDANCE AND RELATED METHODS THEREOF

(71) Applicants: University of Virginia Patent Foundation, Charlottesville, VA (US); Siyong Kim, Glen Allen, VA (US)

(72) Inventors: Taeho Kim, Glen Allen, VA (US); Harang Ju, Charlottesville, VA (US); Siyong Kim, Glen Allen, VA (US)

(73) Assignees: University of Virginia Patent Foundation, Charlottesville, VA (US); Virginia Commonwealth University Intellectual Property Foundation, Richmond, VA (US)

(*) Notice: Subject to any disclaimer, the term of this patent is extended or adjusted under 35 U.S.C. 154(b) by 614 days.

(21) Appl. No.: 15/515,338

(22) PCT Filed: Sep. 29, 2015

(86) PCT No.: PCT/US2015/052975
§ 371 (c)(1),
(2) Date: Mar. 29, 2017

(87) PCT Pub. No.: WO2016/054060
PCT Pub. Date: Apr. 7, 2016

(65) Prior Publication Data
US 2017/0231530 A1 Aug. 17, 2017

Related U.S. Application Data

(60) Provisional application No. 62/233,554, filed on Sep. 28, 2015, provisional application No. 62/057,361, filed on Sep. 30, 2014.

(51) Int. Cl.
*G06K 9/00* (2006.01)
*A61B 5/11* (2006.01)
(Continued)

(52) U.S. Cl.
CPC .......... *A61B 5/1114* (2013.01); *A61B 5/1127* (2013.01); *A61B 5/486* (2013.01);
(Continued)

(58) Field of Classification Search
CPC combination set(s) only.
See application file for complete search history.

(56) References Cited

U.S. PATENT DOCUMENTS

| 8,754,805 B2 | 6/2014 | Wang |
| 2007/0093723 A1 | 4/2007 | Keall |

(Continued)

FOREIGN PATENT DOCUMENTS

| WO | WO 2012/033739 | 3/2012 |
| WO | WO 2013/155394 | 10/2013 |
| WO | WO 2014/116868 | 7/2014 |

OTHER PUBLICATIONS

Arnold et al., "Lung MRI using an MR-compatible active breathing control (MR-ABC)", Magnetic Resonance in Medicine, 2007, pp. 1092-1098, vol. 58.
(Continued)

*Primary Examiner* — Alex Kok S Liew
(74) *Attorney, Agent, or Firm* — Robert J. Decker

(57) ABSTRACT

A system and method for reducing intrafractional motion of a subject The system includes a subject user device, whereby the user device includes an image acquisition device configured to receive location marker information of the subject to provide location marking data of the subject. The system may also include a digital processor configured to: receive the location marking data and determine movement of the
(Continued)

subject relative to the location marker information; and communicate feedback of the movement to the subject to help the subject reduce intrafractional motion.

25 Claims, 7 Drawing Sheets

(51) Int. Cl.
- A61N 5/10 (2006.01)
- A61B 5/00 (2006.01)
- A61B 5/113 (2006.01)
- A61B 5/055 (2006.01)
- A61B 90/00 (2016.01)

(52) U.S. Cl.
CPC ........... *A61N 5/107* (2013.01); *A61N 5/1049* (2013.01); *A61B 5/0555* (2013.01); *A61B 5/113* (2013.01); *A61B 2090/3937* (2016.02); *A61N 2005/1059* (2013.01)

(56) References Cited

U.S. PATENT DOCUMENTS

| | | | |
|---|---|---|---|
| 2007/0110289 A1* | 5/2007 | Fu | A61B 6/4458 382/128 |
| 2010/0151416 A1 | 6/2010 | Kim | |
| 2010/0245360 A1* | 9/2010 | Song | A61B 5/02007 345/441 |
| 2011/0172526 A1* | 7/2011 | Lachaine | A61B 34/20 600/439 |
| 2013/0289796 A1 | 10/2013 | Bergfjord | |
| 2015/0009029 A1* | 1/2015 | Martin | A61B 5/7405 340/539.15 |

OTHER PUBLICATIONS

Bentel et al., "Comparison of Two Head and Neck Immobilization Systems", International Journal of Radiation Oncology & Biology Physics, 1997, pp. 867-873, vol. 38, No. 4.

Dunn et al., "A programmable motion phantom for quality assurance of motion management in radiotherapy," Australasian Physical & Engineering Sciences in Medicine, 2012, pp. 93-100, vol. 35.

George et al., "Audio-visual Biofeedback for Respiratory-gated Radiotherapy: Impact of Audio Instruction and Audio-visual Biofeedback on Respiratory-gated Radiotherapy", International Journal of Radiation Oncology & Biology Physics, 2006, pp. 924-933, vol. 65, No. 3.

Huda et al., "Patient size and x-ray technique factors in head computed tomography examinations. I. Radiation doses", Medical Physics, online Mar. 2004, pp. 588-594, vol. 31, No. 3.

Ju et al., "Development of a novel remote-controlled and self-contained audiovisual-aided interactive system for immobilizing claustrophobic patients", Journal of Applied Clinical Medical Physics, 2015, pp. 216-224, vol. 16, No. 3.

Keall et al., "The management of respiratory motion in radiation oncology report of AAPM Task Group 76", Medical Physics, 2006, pp. 3874-3900, vol. 33, No. 10.

Kim et al., "Audiovisual biofeedback improves diaphragm motion reproducibility in MRI", Medical Physics, 2012, pp. 6921-6928, vol. 39, No. 11.

Kim et al., "Double-Ends Quasi-Breath-Hold (DE-QBH) Technique for Respiratory Motion Management", (Abstract) Medical Physics, 2013, 3 pages, vol. 40, Iss. 6, Part 16.

Kim et al., "Laser-Guided Interactive Patient Immobilization System for the Brain or Head and Neck Treatment", Medical physics; ICMP (14th), 2005, pp. 838-839 (2 pages).

Kim et al., "Quasi-breath-hold (QBH) Biofeedback in Gated 3D Thoracic MRI: Feasibility Study", Progress in Medical Physics, 2014, pp. 72-78, vol. 25, No. 2.

Kim et al., "An Immobilization System for Claustrophobic Patients in Head-and-Neck Intensity-Modulated Radiation Therapy", International Journal of Radiation Oncology & Biology Physics, 2004, pp. 1531-1539, vol. 59, No. 5.

Li et al., "Migration from full-head mask to "open-face" mask for immobilization of patients with head and neck cancer", Journal of Applied Clinical Medical Physics, 2013, pp. 243-254, vol. 14, No. 5.

Lim et al., "Guiding curve based on the normal breathing as monitored by thermocouple for regular breathing", Medical Physics, 2007, pp. 4514-4518, vol. 34, No. 11.

McKenna et al., "Tracking colour objects using adaptive mixture models", Image and Vision Computing, 1999, pp. 225-231, vol. 17.

Park et al., "Quasi-breath-hold technique using personalized audio-visual biofeedback for respiratory motion management in radiotherapy", Medical Physics, 2011, pp. 3114-3124, vol. 38, No. 6.

Publicover et al., "SU-GG-T-305: Feasibility of Using a Programmable Respiratory Motion Phantom for Qa and Assessment of Dosimetric Implications of Breathing Motion During Radiation Therapy", (Abstract), Medical Physics, 2008, pp. 2795-2795, vol. 35, Iss. 6, Part 14.

Varian Medical Systems, "Real-time Position Management System; Comprehensive System for Total Motion Management", Brochure (online), 2007 (retrieved Nov. 16, 2015), 8 pages, retrieved from the Internet <URL: https://www.varian.com/sites/defauiVfiles/resource_attachments/RPMSystemProductBrief_RAD 5614B_August2007.pdf>.

Venkat et al., "Development and preliminary evaluation of a prototype audiovisual biofeedback device incorporating a patient-specific guiding waveform", Physics in Medicine and Biology, 2008, pp. N197-N208, vol. 53.

Xing et al., "Dosimetric effects of patient displacement and collimator and gantry angle misalignment on intensity modulated radiation therapy", Radiotherapy and Oncology, 2000, pp. 97-108, vol. 56.

Yamamoto et al., "Retrospective Analysis of Artifacts in Four-Dimensional CT Images of 50 Abdominal and Thoracic Radiotherapy Patients", International Journal of Radiation Oncology & Biology Physics, 2008, pp. 1250-1258, vol. 72, No. 4.

\* cited by examiner

INTRAFRACTIONAL MOTION REDUCTION SYSTEM USING AUDIOVISUAL-AIDED INTERACTIVE GUIDANCE AND RELATED METHODS THEREOF

CROSS-REFERENCE TO RELATED APPLICATIONS

The present application is a national stage filing of International Application No. PCT/US2015/052975, filed Sep. 29, 2015, which claims benefit of priority under 35 U.S.C. § 119(e) from U.S. Provisional Application Ser. No. 62/057,361, filed Sep. 30, 2014, entitled "Personal Digital Assistant (PDA) with Retina Display for Intrafractional Motion Reduction as a Remote-Controlled and Self-Contained Audiovisual Biofeedback System" and U.S. Provisional Application Ser. No. 62/233,554, filed Sep. 28, 2015, entitled "Personal Digital Assistant (PDA) with Retina Display for Intrafractional Motion Reduction as a Remote-Controlled and Self-Contained Audiovisual Biofeedback System"; the disclosures of which are hereby incorporated by reference herein in their entirety.

FIELD OF THE INVENTION

The present invention relates generally to the field of managing intrafractional motion. More specifically, the invention relates to the subfield and using a self-contained audiovisual-aided interactive system.

BACKGROUND

Patient motion is one of prevalent concerns in medical imaging and radiation treatment delivery.[1] (See L. Xing, Z.-X. Lin, S. S. Donaldson, Q. T. Le, D. Tate, D. R. Goffinet, S. Wolden, L. Ma, A. L. Boyer, "Dosimetric effects of patient displacement and collimator and gantry angle misalignment on intensity modulated radiation therapy," Radiotherapy and Oncology 56, 97-108 (2000), of which is incorporated by reference herein.) If not properly managed during radiotherapy, it can result in insufficient dose delivery to the target and/or unnecessary irradiation of surrounding healthy tissues. A number of diverse motion management techniques have been proposed for various disease sites such as simple face mask, bite block, and more aggressive head-frame for brain/H&N (head and neck) immobilization,[2-4] and motion-encompassing, active breath control, and real-time tumor tracking for breathing motion management.[5, 6] Moreover, most of the motion management systems are intolerable for claustrophobic patients. For example, only a few immobilization systems such as open-face mask and head mold with a bite plate are available for the claustrophobic patients, but they are mainly mask-based and make the patients passive recipient of care with a certain degree of discomfort. (See G. Li, D. M. Lovelock, J. Mechalakos, S. Rao, C. Della-Biancia, H. Amols, N. Lee, "Migration from full-head mask to "open-face" mask for immobilization of patients with head and neck cancer," Journal of Applied Clinical Medical Physics 142013, of which is incorporated by reference herein).

While most motion management techniques are mainly operator driven, there are evidences that patient interactive (or biofeedback) mechanism can enhance their performance. The concept of patient interactive immobilization for brain/H&N was first introduced by Kim and Helmig,[7] and Kim et al. demonstrated feasibility of the concept using a simple laser-based device.[8] Similar approaches, under the name of audiovisual (AV) biofeedback, have been widely studied for the management of tumor movement caused by respiratory motion.[6, 9, 10] For instance, several research groups demonstrated that AV biofeedback could significantly reduce respiratory irregularities during medical imaging or radiation treatment.[6, 9, 10] Lim et al. also showed significant improvements in breathing motion regularities through a visual guidance system.[11] Additionally, Arnold et al. decreased respiratory motion artifacts in MRI through active breath control (ABC).[12] An interesting concept of quasi-breathhold (QBH) was also possible by virtue of AV biofeedback.[13, 14]

Though these studies have demonstrated improvements in intrafractional motion management, most systems employ tools that are relatively complicated and costly, which causes certain extent of limitation in their accessibility by patients and flexibility in clinical use. For example, AV biofeedback often utilizes the real-time positioning management (RPM) system (Varian Medical Systems, Palo Alto, USA) for motion tracing, and the breath-regulation system by Lim et al. requires a respiration-monitoring mask together with a thermocouple. The ABC system utilized by Arnold et al. also necessitates a spirometer and a pneumotachograph.

The disclosed system is directed toward improving the efficiency and related complications of managing intrafractional motion.

Overview

In radiotherapy, one of prevalent concerns for accurate treatment delivery is voluntary movement by the patient. An aspect of an embodiment of the present invention provides, but not limited thereto, a remote-controlled and self-contained audiovisual (AV)-aided interactive system with the personal digital assistant (PDA) (such as an iPad mini or the like; as well as other processor based systems or other machine as desired or required) with Retina display, easily obtainable and cost-effective tablet computers, for intrafractional motion reduction in brain/H&N (head and neck) radiotherapy.

An aspect of an embodiment of the present invention provides, but not limited thereto, a system for reducing intrafractional motion of a subject. The system may comprise a subject user device, whereby the user device may comprise an image acquisition device configured to receive location marker information of the subject to provide location marking data of the subject. The system may comprise: a digital processor configured to: receive the location marking data and determine movement of the subject relative to the location marker information; and communicate feedback of the movement to the subject to help the subject reduce intrafractional motion.

An aspect of an embodiment of the present invention provides, but not limited thereto, a computer implemented method for reducing intrafractional motion of a subject. The method may comprise: receiving location marker information of the subject and generating location marking data of the subject; digitally processing the location marking data and determining movement of the subject relative to the location marker information; and communicating feedback of the movement to the subject to help the subject reduce intrafractional motion.

An aspect of an embodiment of the present invention provides, but not limited thereto, a non-transitory machine readable medium including instructions for reducing intrafractional motion of a subject, which when executed by a machine, cause the machine to: receive location marker information of the subject and generate location marking data of the subject; determine movement of the subject relative to the location marker information; and transmit to an output module to communicate feedback of the movement to the subject to help the subject reduce intrafractional motion.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS OF THE PRESENT INVENTION

Figure 1:
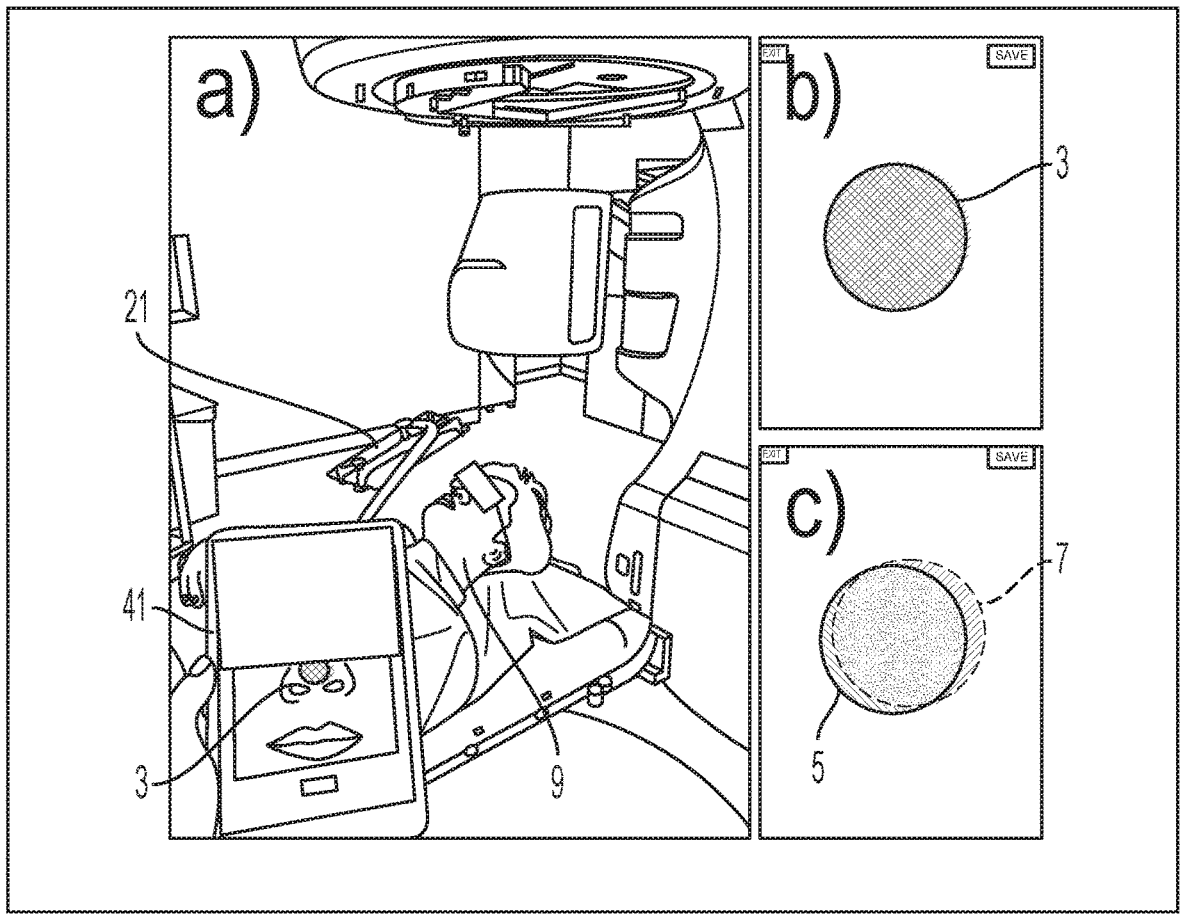
FIG. 1(A) is an illustration of a self-contained AV-aided interactive system of iPad minis with Retina display that is shown with the session setup. The AV-aided interactive tablet (or AV-guidance tablet) and the remote control tablet are shown at the treatment room.
FIG. 1(B) is an illustration of a green disk over top of a blue disk (not shown) that was shown at the center of the display as a reference for the guiding disk.
FIG. 1(C) is an illustration of the color of the circle gradually transitioned from green to red as the motion delta increases from zero to a predetermined warning distance (for example, 2 mm for this study).

In an approach, the self-contained AV-aided interactive system (and related method and computer readable medium) utilized two tablet computers: one for audiovisual guidance for the subject and the other for remote control by an operator. The tablet for audiovisual guidance traced the motion of a colored marker using the built-in front-facing camera, and the remote control tablet at the control room used infrastructure Wi-Fi networks for real-time communication with the other tablet (tablet for the audiovisual guidance). The marker was traced using a color-based motion-tracking algorithm. In an evaluation, a programmed QUASAR motion phantom was used to test the temporal and positional accuracy and resolution. In addition, position data were also obtained from eight healthy volunteers in two studies (one study with one marker and other with two markers) with and without guidance to evaluate the reduction of intrafractional head motion.

An aspect of an embodiment of the present invention provides, but not limited thereto, a personal digital assistant (PDA) with retina display for intrafractional motion reduction as a remote-controlled and self-contained audiovisual-aided interactive system.

As disclosed herein, a purpose of a study by the present inventors, among other things, was to develop and evaluate a novel remote-controlled and self-contained AV-aided interactive tool using easily obtainable and cost-effective tablet computers (or other processor based systems or other machines as desired or required). For instance, two iPad minis with Retina display (Model A1489; Apple Inc., Cupertino, USA) were chosen and mobile applications were developed to provide a more accessible and flexible platform for AV-aided interactive guidance for minimizing intrafractional motion. For feasibility test purpose, the performance of the system was investigated in terms of resolution, accuracy, and its effectiveness on intrafractional head motion management of human subjects simulating a claustrophobic brain or H&N case were evaluated.

An aspect of an embodiment of the present invention included a study providing a real-time remote-controlled audiovisual-aided interactive guidance that was achieved using a self-contained system of tablet computers. In the phantom study, the temporal and positional resolution was 24 Hz and 0.2 mm. In the volunteer study, the average vertical and horizontal displacement was reduced from 3.2 mm to 0.4 mm and from 1.3 mm to 0.3 mm with audiovisual guidance, respectively. The vertical and horizontal baseline shift was reduced from 0.8 mm/min to 0.06 mm/min and from 0.3 mm/min to 0.06 mm/min with audiovisual guidance. This study demonstrated, among other things, a reduction in intrafractional head motion using a remote-controlled and self-contained audiovisual (AV)-aided interactive system of PDAs (such as iPad minis, or other types of tablets or the like) with Retina display, easily obtainable and cost-effective tablet computers. This system and related method can streamline clinical flow with the proposed remote-controlled and self-contained system and by allowing patients to practice self-motion management before radiation treatment delivery.

An aspect of an embodiment of the present invention included a study whereby in the evaluation, a programmed QUASAR motion phantom was used to test the temporal and position accuracy and resolution. Position data were also obtained from ten healthy volunteers with and without guidance to evaluate the reduction of intrafractional head motion in simulations of a claustrophobic brain or H&N case. In the phantom study, the temporal and positional resolution was 24 Hz and 0.2 mm. In the volunteer study, the average superior-inferior and right-left displacement was reduced from 3.2 mm to 0.4 mm and from 1.3 mm to 0.2 mm with AV-aided interactive guidance, respectively. The superior-inferior and right-left positional drift was reduced from 0.8 mm/min to 0.1 mm/min and from 0.3 mm/min to 0.1 mm/min with audiovisual-aided interactive guidance. This study demonstrated a reduction in intrafractional head motion using a remote-controlled and self-contained AV-aided interactive system of iPad minis with Retina display, easily obtainable and cost-effective tablet computers. This approach can streamline clinical flow for claustrophobic patients without a head mask and by allowing patients to practice self-motion management before radiation treatment delivery.

In an aspect of an embodiment of the present invention, of which may be referenced by FIG. 1(A), as a general but non-limiting approach, provided is a system for reducing intrafractional motion of a subject 9. The system may comprise a subject user device 21 that includes an image acquisition device configured to receive location marker information of the subject 9 to provide location marking data of the subject 9. In an embodiment, the subject user device 21 may comprise an AV Guidance tablet. The digital processor may be configured to receive the location marking data and determine movement of the subject 9 relative to the location marker information. The digital processor may be further configured to communicate feedback of the movement to the subject 9 to help the subject 9 reduce intrafractional motion. The communication feedback to the subject 9 may be accomplished in real time. The communication feedback of the movement to the subject 9 may be include a visual display, audio signal, or both visual and audio. The visual display may be a display panel disposed in or in communication with the subject user device 21 and which is viewable by the subject 9. The visual display may be an AV Guidance tablet disposed in or in communication with the subject user device 21 and which is viewable by the subject 9. The digital processor determines a reference point and a movement point, whereby the reference point represents a starting position of the subject 9; and the movement point represents an indication of intrafractional motion of the subject 9. The display panel may include a display reference point and a display movement point, whereby reference point represents to a subject a starting position of the subject 9; and the display movement point represents to a subject an indication of intrafractional motion of the subject 9. The display reference point may be a first color having a preselected pattern, and the display movement point may be a second color having a preselected pattern, whereby the intrafractional motion causes the display movement point to move relative to the reference point, and that which is discernable to the subject 9. The audio signal may be provided by a speaker in communication with the subject user device 21 and which is audible to the subject 9. The system may further include an operator device 41. The operator device 41 may include an operator digital processor configured to communicate with the subject user device 21. The operator digital processor is configured to control and/or monitor the subject user device 21. The operator device 41 may include at least one of the following: video display, alpha-numeric input device, or UI navigation device for controlling or monitoring the subject user device 21. Similarly, subject user digital processor may be configured to control the subject user device 21. The location marker information of the subject 9 is provided by the following: a marking substrate that is disposed on the subject; a location that is identified on the subject; or a combination of disposing a marking substrate on the subject and identifying a location on the subject. Alternatively, the determination of movement of the subject may be provided by the processor configuring a geometric representation of rotation of the head of the subject. For example, the geometric representation of rotation of the head of the subject (or may be other region(s) of the subject as desired, required, or needed) is provided according to the following characteristics: h, wherein h is the length of the head from the forehead to the back of the head, δ, wherein δ is the symbol of linear displacement, c, wherein c is the distance from the image acquisition device (e.g., camera) to a marker at δ=0, Δ, wherein Δ is the actual linear displacement of the marker caused by the head rotation of θ, Φ, wherein Φ is the angle of the image acquisition device seeing the displaced marker, d, wherein d is the distance from the acquisition device to the marker at δ=Δ, and Ω, wherein Ω is the calculated displacement by the system.

Figure 5:
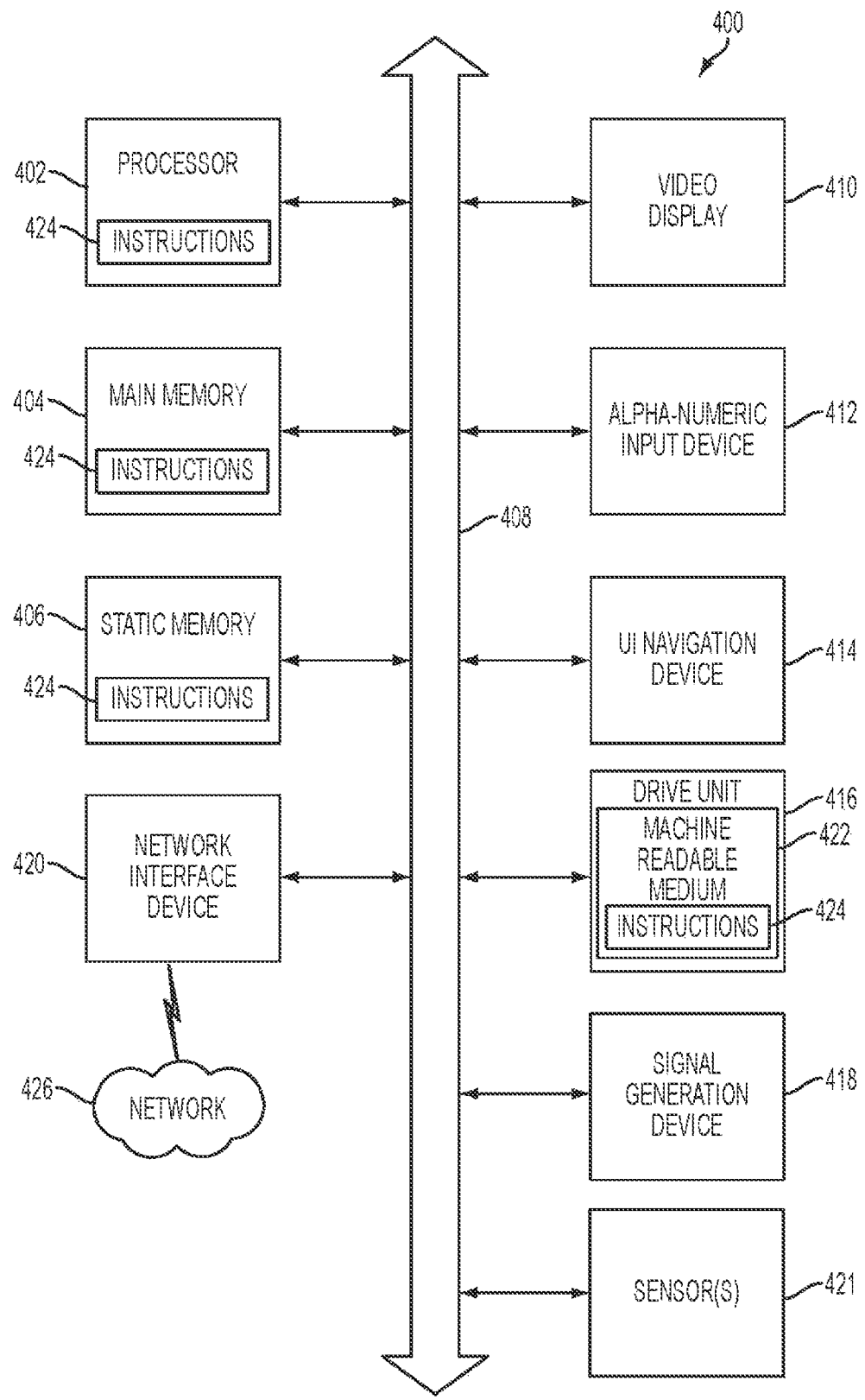
FIG. 5 is a block diagram illustrating an example of a machine upon which one or more aspects of embodiments of the present invention can be implemented.

FIG. 5 is a block diagram illustrating an example of a machine upon which one or more aspects of embodiments of the present invention can be implemented.

FIG. 5 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410 (or audio unit), an alphanumeric input device 412 (e.g., a keyboard), and a user interface (UI) navigation device 414 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, image acquisition or recording device, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

EXAMPLES

Practice of the invention will be still more fully understood from the following examples and experimental results, which are presented herein for illustration only and should not be construed as limiting the invention in any way.

Example and Experimental Results Set No. 1

Methods and Materials
A. Self-Contained AV-Aided Interactive System

An aspect of an embodiment of the present invention system that was developed includes, but not limited thereto, two tablet computers (iPad minis with Retina display, Model A1489). One unit (i.e., iPad mini #1) provides AV-aided interactive guidance to the subject inside the treatment/simulation room, and the other unit (i.e., iPad mini #2) is used for remotely controlling the AV-aided interactive device (i.e., iPad mini #1).

For interactive guidance, 1) a marker (colored and non-reflective) is attached on the skin of the patient, 2) the unit #1 continuously captures the image of the marker (in 1280-by-720 resolution using the built-in front-facing FaceTime HD camera), 3) image analysis is carried out by the application developed to determine the position of the marker (consequently that of the patient), and 4) both the current and reference marker positions are displayed so that the patient can feedback in real-time.

The marker position is determined by filtering the background based on the marker's color;[15] and a green or blue marker is preferred to maximize signal-to-noise ratio. Both image processing and analysis are done with OpenCV for iOS (version 2.4.9, supported by Willow Garage and Itseez). The calculations are done in pixels first then converted to millimeters. For the pixel-to-mm conversion, a mm-to-pixel ratio is obtained with the marker's maximum length in pixels measured by the camera and a predetermined length in mm. For example, the millimeter-to-pixel ratio was 0.1 mm/pixel at 14 cm and 0.2 mm/pixel at 25 cm. The motion data is then relayed to the subject through AV-aided interactive guidance in real-time on the same tablet unit.

For visual feedback, the tablet displays the horizontal (x-direction) and vertical (y-direction) components of the real-time motion delta by translating a translucent disk on the iPad's display (2048-by-1536 resolution) as shown in FIG. 1(A). A blue disk (not shown as it's covered by a green disk 3) is shown at the center of the display as a reference for the guiding disk. To ease the cognitive load of the perception of the motion delta's magnitude, the color of the circle gradually changes from green 3 (as shown in FIG. 1(B)) to red 7 as the motion delta increases from 'zero' to a predetermined warning distance (2 mm for this study) as illustrated in FIG. 1(C). Partial view of the blue disk 5 can be observed in FIG. 1(C). It should be appreciated that various colors, designs, shapes and patterns may be implemented as desired, required, or needed—as well as their associated sequence timing.

The audio component of AV-aided interactive system produces short beeps that gradually increase in frequency as the motion delta from the reference point becomes larger. When motion delta is smaller than 10% of the designated warning distance, no beeps are generated. When the motion delta reaches to and becomes greater than the designated warning distance, the frequency of beeps gets plateaued. It should be appreciated that various audio tones, pitches, and volumes may be implemented as desired, required, or needed—as well as their associated sequence timing.

B. Evaluation of Basic Characteristics

The positional accuracy and resolution of the system were investigated through a phantom study using a programmable QUASAR motion phantom (Modus Medical Devices Inc., London, Canada) 61 shown in FIG. 2(A). The reference marker was moved with three different positions (10 mm, 20 mm and 30 mm) using the programmed QUASAR motion phantom 61 while the motion was detected and recorded by the tracking device. Tests were made in three different levels of marker used, such as one marker, two markers with parallel or perpendicular motion and three markers with the triangular configuration: 15 cm of the marker plane-to-camera distance. The temporal accuracy and resolution of the system were studied with the QUASAR motion phantom 61 which was set to oscillate with a peak-to-peak amplitude of 10 mm in a five second period. The temporal accuracy was determined by averaging all peak-to-peak periods measured by the system. Referring to FIGS. 2(B) and 2(C), the AV-aided interactive tablet measured the horizontal (x-direction) and vertical (y-direction) components, respectively, of the real-time motion and showed the mean displacement with horizontal and vertical data separate after the session.

C. Feasibility Test with Human Subjects

A feasibility study for intrafractional head motion management was performed to investigate the effectiveness of the system. To be conservative, simulation was carried out under the assumption that patients were claustrophobic, meaning completely no immobilization device other than a headrest provided.

Eight healthy volunteers (age: 30.2±11.2, age range: 20~52) participated in the study and their voluntary head motion reduction with AV-aided interactive guidance was evaluated. Each study consisted with two sessions with and without guidance to compare the intrafractional head motion. Each session lasted for 5 minutes in the TrueBeam treatment room for the first study with one marker and in the CT simulation room for the second study with two markers. The AV-aided interactive guidance tablet (i.e., unit #1) was placed above the subject's head (using a flexible tablet arm) for audiovisual guidance and the tracking marker (green colored) was placed on the nose of the subject as shown in FIG. 1(A) (as can be observed on the display of the operator device 41 (e.g., remote control tablet)) for the first study (five volunteers). For the second study with two markers, the tracking markers were placed on the nose of the subject and the area between the eyebrows (five volunteers: two of five volunteers participated in the first study (vol1 and vol2)). The other tablet (i.e., unit #2) was utilized for real-time remote controlling and monitoring (both can be performed within and outside the study room) during the session. Just for comparison purpose, each participant performed one more session without AV-aided interactive guidance. In the sessions without guidance, the system collected motion data, and AV-aided interactive guidance was not given to the subject. The mean displacement was calculated by averaging the absolute values of the displacements (with horizontal and vertical data separate), and the baseline shift was calculated by employing a linear fit on the displacements to determine the mm per minute baseline shift.

Results

A. Basic Characteristics

The mean variation in positional accuracy was 0.3 mm independent on the number of markers, and the mean positional resolution was 0.2 mm. The mean variation in temporal accuracy was less than 0.6 ms, and the mean temporal resolution was 24 Hz (42 ms per data point—shown in the illustration of FIG. 2).

B. Feasibility Test with Human Subjects

Figure 3:
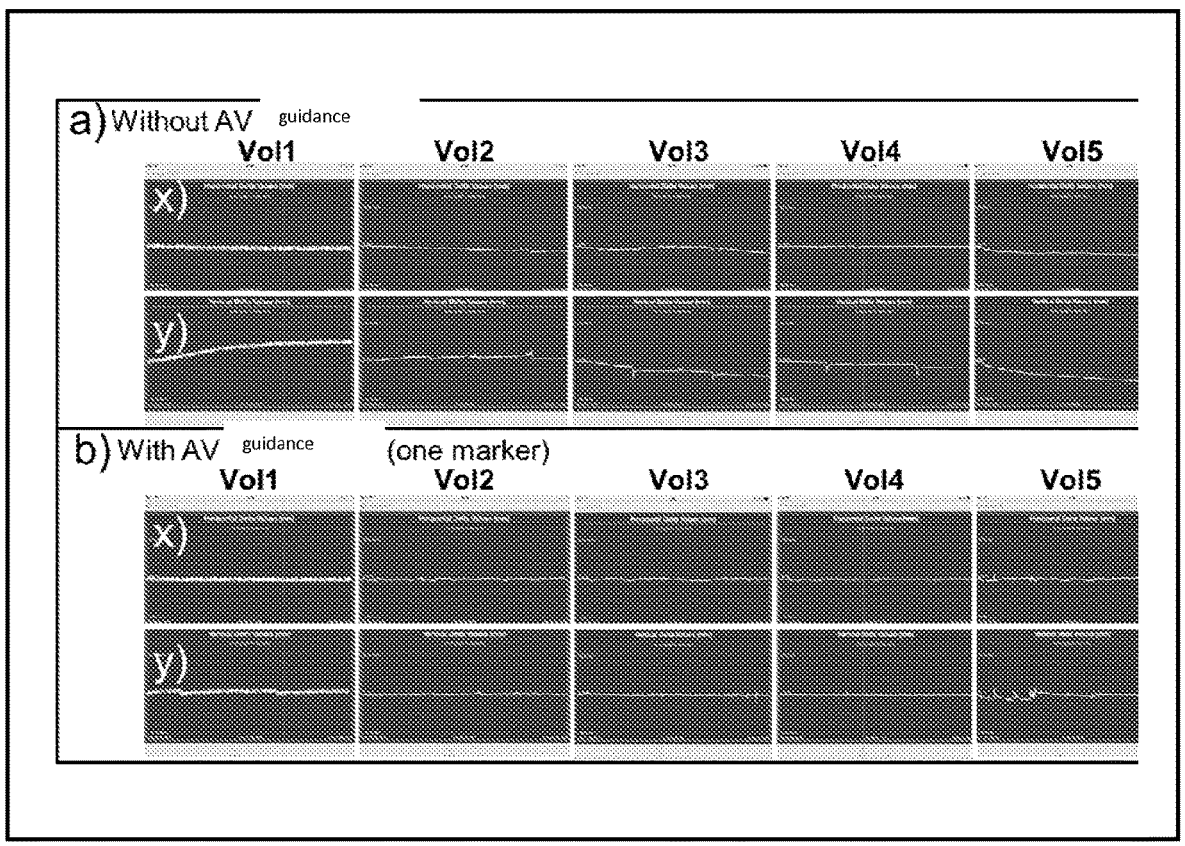
FIGS. 3 (A) and 3(B) are screenshots pertaining to the first study with one marker whereby the intrafractional voluntary head motions of five volunteers with one marker are graphically shown without AV-aided interactive guidance and with AV-aided interactive guidance, respectively. The mean displacement decreased vertically by an average of 88% and horizontally by an average of 77% with AV guidance.

In the first study with one marker, intrafractional voluntary head motion, in average, was kept within 0.5±0.4 mm and 0.3±0.1 mm for vertical- and horizontal-direction with guidance, respectively (see FIG. 3), showing very promising performance while those without guidance were 4.2±2.5 mm (vertically) and 1.3±1.2 mm (horizontally). Compared to the case of no-guidance, the mean displacement was decreased vertically by an average of 88% and horizontally by an average of 77%. Noticeable positional drift was also observed in the sessions without AV-aided interactive guidance. The average drift was decreased with AV guidance from 1.1±0.7 mm/min to 0.1±0.1 mm/min (91% reduction) vertically and from 0.3±0.2 mm/min to 0.1±0.1 mm/min (66% reduction) horizontally.

Figure 4:
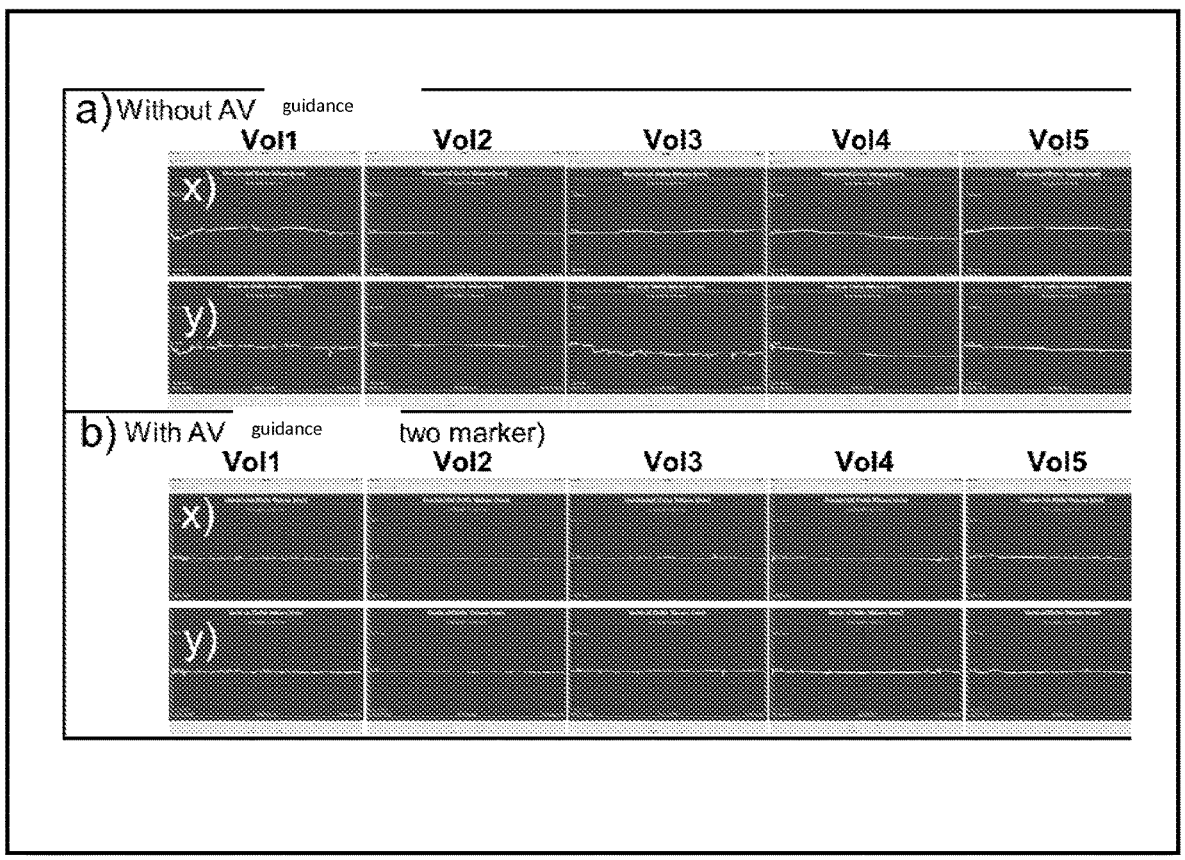
FIGS. 4(A) and 4(B) are screenshots pertaining to the second study with two markers whereby the intrafractional voluntary head motions of five volunteers with two markers are shown without AV-aided interactive guidance and with AV-aided interactive guidance, respectively. The mean displacement decreased vertically by an average of 90% and horizontally by an average of 83% with AVguidance.

In the second study with two markers, average intrafractional voluntary head motion was 0.2±0.01 mm and 0.2±0.1 mm for vertical- and horizontal-direction with guidance, respectively (see FIG. 4): 2.1±1.6 mm (vertically) and 1.2±0.6 mm (horizontally) without guidance. The mean displacement was decreased vertically by an average of 90% and horizontally by an average of 83% using the AV-aided interactive guidance. Positional drift was also observed without AV-aided interactive guidance. The average drift decreased from 0.4±0.3 mm/min to 0.01±0.01 mm/min (95% reduction) vertically and from 0.3±0.3 mm/min to 0.01±0.01 mm/min (86% reduction) horizontally with AV-aided interactive guidance.

In the average displacement with two studies, it was reduced from 3.2 mm to 0.4 mm (vertical) and from 1.3 mm to 0.3 mm (horizontal) with audiovisual guidance, respectively. In addition, the vertical and horizontal baseline shift was reduced from 0.8 mm/min to 0.06 mm/min (vertical) and from 0.3 mm/min to 0.06 mm/min (horizontal) with audiovisual guidance.

Discussion

In this study, a remote-controlled and self-contained audiovisual-aided interactive system of iPad minis with Retina display was developed and evaluated for intrafractional motion management. The system was tested using the programmed QUASAR motion phantom in its resolution and accuracy in both positional and temporal aspects, and showed satisfactory performance (e.g., 0.2 mm positional resolution and 0.6 ms temporal resolution). When applied for human subjects, the system was able to keep intrafractional head motion within a range acceptable for high precision (in average, 0.5 mm and 0.3 mm for vertical- and horizontal-direction in the first study and 0.2 mm and 0.2 mm for vertical- and horizontal-direction in the second study, respectively).

This system and related method provides benefits as a self-contained system of tablet computers. It can be easily accessible by patients, and they could potentially practice AV-aided interactive guidance using their own personal device(s) at the waiting room or even at home. Note that the AV-aided interactive guidance tablet can be used with complete functionality without the remote control tablet. In addition, any iOS device, including iPhone and iPod, can substitute both the AV-aided interactive guidance and remote control components. The system is very easy to use (with most patients being familiar with iOS devices) and requires relatively simple setup thus, can be implemented without difficulty in most clinics even including places where resources are limited. As mentioned, if the system is installed in waiting areas for patients to practice before they begin radiation therapy treatments or CT simulation, it would improve not only delivery accuracy but also work flow efficiency.

The system utilizes tablet's built-in front-facing camera to detect motion and consequently is constrained by the inherent resolution and limitations of the camera. The system showed an error range of one pixel, and the corresponding error in millimeters depended on the distance from the camera to the marker. For example, the millimeter-to-pixel ratio was 0.1 mm/pixel at 14 cm and 0.2 mm/pixel at 25 cm. At greater distances, the positional resolution of the system would decrease. However, in practice, it is not likely to have such long distance. As long as the camera is within 50 cm distance, under 1 mm resolution can be easily obtained. In addition, 10 mm head motion with 3 degree rotation can be detected with 0.17% error by the system (20 cm away from the marker).

In this study, the system tracked a single marker or two markers on the subject's face and detected two translational degrees of freedom. In a 3-dimensional space, three translational planes and three rotational axes exist thus, the 2-dimensional motion detection of the system did not reflect true 3-dimensional motion. However, the tablet was close in distance to the subject's head, and the subjects were limited in their movements by the physiology of the human head and neck in lay-down position. Therefore, we believe, 2-dimensional motion detection would be sufficient for intrafractional head motion reduction in the current use case. To extend functionality for other use cases, if it is absolutely necessary, the system could utilize mobile 3D cameras for 3-dimensional motion tracing with the cost of adding little more complexity.

An aspect of an embodiment of the present invention system may include, but not limited thereto, two tablets, one for both motion tracing and audiovisual guidance, and the other for remote control. With a router outside the treatment room wired to an access point inside the room, an infrastructure Wi-Fi can be created and both tablets can communicate with each other between the treatment and control rooms. The AV-aided interactive tablet streams frames captured from the front-facing camera to the remote control tablet and can potentially transmit other useful information that can be easily monitored by the remote control tablet. Another benefit of an embodiment of the system, among others, is that only a single small mobile device is required in the treatment room for AV-aided interactive guidance, and the remote control device can communicate with the AV-aided interactive tablet anywhere outside of the treatment room. Although the system is extremely simple and cost-effective compared to most commercially available motion management systems such as ExacTrac infrared camera system (BrainLab, Feldkirchen, Germany), AlignRT (Vision RT, Columbia, USA), RPM system, and ABC (Elekta, Stockholm, Sweden), it demonstrated a kind of unique and sufficient functionality of AV-aided interactive guidance.

For smooth clinical implementation, a similar feasibility study with an actual patient group is under consideration.

Conclusion

This study developed and demonstrated a self-contained AV-aided interactive system (and related method and computer readable medium) using easily obtainable and cost-effective tablet computers, with the iPad mini with Retina display. This approach can streamline clinical flow with the proposed remote-controlled and self-contained system and by, among other things, allowing patients to practice self-motion management before radiation treatment delivery.

Example and Experimental Results Set No. 2

Methods and Materials

A. Self-Contained AV-Aided Interactive System

Refer to section above also referenced as "A. Self-contained AV-aided interactive system".

B. Evaluation of Basic Characteristics

Figure 2:
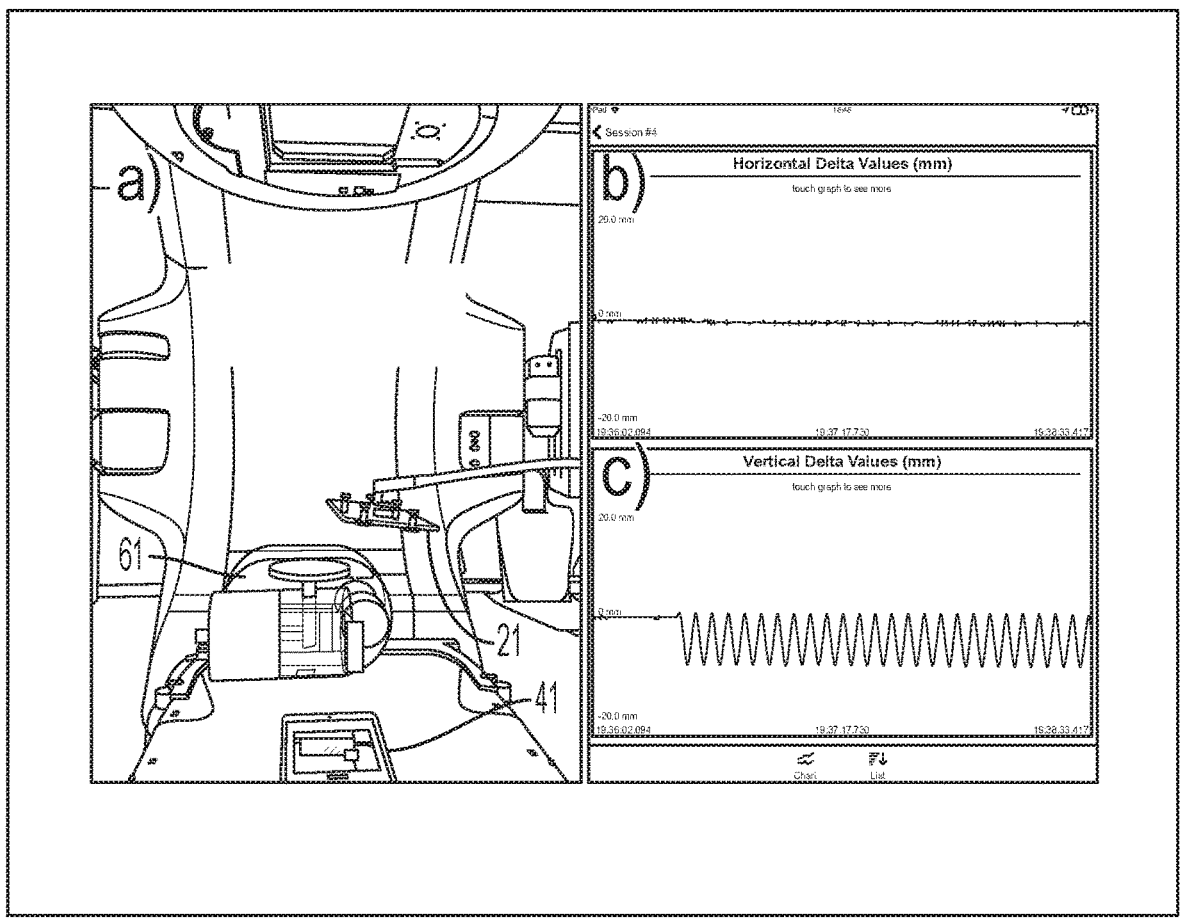
FIG. 2(A) is an illustration of a set up of the temporal accuracy and resolution that was studied with the QUASAR motion phantom, which included the AV-aided interactive tablet (or AV-guidance tablet) and remote control tablet.
FIGS. 2(B) and 2(C) are illustrations that graphically depict the horizontal (x-direction) and vertical (y-direction) components, respectively, of the real-time motion as measured by the AV-aided interactive tablet; and showed the mean displacement with horizontal and vertical data separate after the session.

The positional accuracy and resolution of the system were investigated through a phantom study using a programmable QUASAR motion phantom (Modus Medical Devices Inc., London, Canada) which is suitable for QA and assessment of motion with sub-millimeter accuracy shown in FIG. 2. (See J. Publicover, A. Vandermeer, B. Norrlinger, H. Alasti, "SU-GG-T-305: Feasibility of Using a Programmable Respiratory Motion Phantom for QA and Assessment of Dosimetric Implications of Breathing Motion During Radiation Therapy," Medical Physics 35, 2795-2795 (2008) and L. Dunn, T. Kron, P. Johnston, L. McDermott, M. Taylor, J. Callahan, R. Franich, "A programmable motion phantom for quality assurance of motion management in radiotherapy," Australasian Physical & Engineering Sciences in Medicine 35, 93-100 (2012); both disclosures of which are incorporated by reference herein.) The marker was moved with three different positions (10 mm, 20 mm and 30 mm) using the programmed QUASAR motion phantom while the motion was detected and recorded by the tracking device. Tests were made in 15 cm, 30 cm and 50 cm of the marker plane-to-camera distance with parallel (right-left) or perpendicular (superior-inferior) motion.

The temporal accuracy and resolution of the system were studied with the QUASAR motion phantom which was set to oscillate with a peak-to-peak amplitude of 10 mm in a five second period. The temporal accuracy was determined by averaging all peak-to-peak periods measured by the system.

Figure 6:
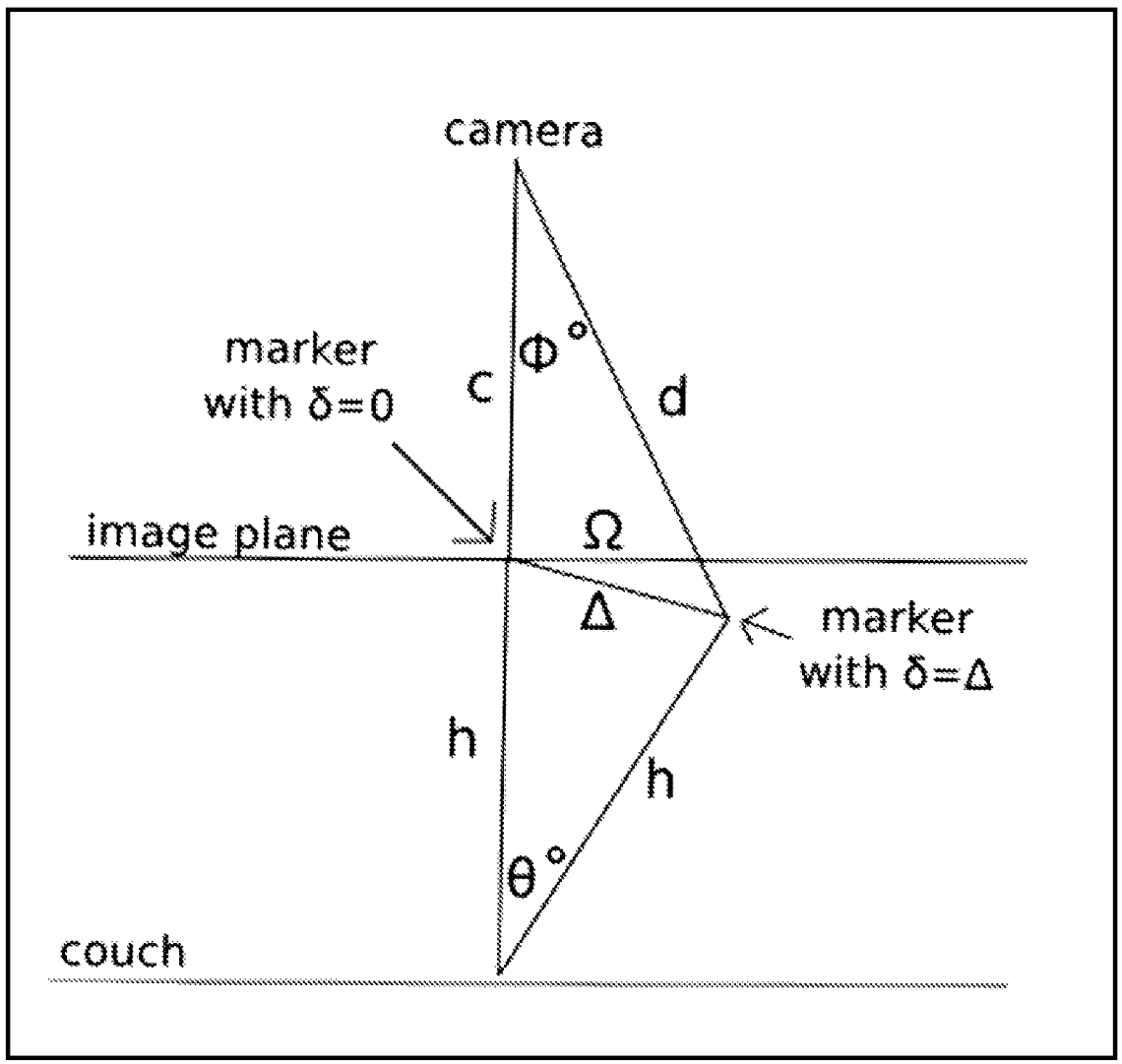
FIG. 6 provides a screenshot of a geometric representation of the patient's head rotation with respect to the camera, assuming that the back of the head is anchored by the head rest, where h is the length of the head from the forehead to the back of the head, $\delta$ is the symbol of linear displacement, c is the distance from the camera to the marker at $\delta=0$, $\Delta$ is the actual linear displacement of the marker caused by the head rotation of $\theta$, $\Phi$ is the angle of the camera seeing the displaced marker, d is the distance from the camera to the marker at $\delta=\Delta$, and $\Omega$ is the calculated displacement by the system.

The error resulting from rotational head movements detected by a two-dimensional camera was simulated in most use cases of the system. A geometric representation of the patient's head rotation with respect to the camera, assuming that the back of the head is anchored by the head rest, is shown in the screenshot of FIG. 6, where h is the length of the head from the forehead to the back of the head, $\delta$ is the symbol of linear displacement, c is the distance from the camera (e.g., image acquisition device) to the marker at $\delta=0$, $\Delta$ is the actual linear displacement of the marker caused by the head rotation of $\theta$, $\Phi$ is the angle of the camera seeing the displaced marker, d is the distance from the camera to the marker at $\delta=\Delta$, and $\Omega$ is the calculated displacement by the system. It is noted that c, the distance from the camera to the marker at $\delta=0$ is assumed to be 20 cm, and h, the length of the head is assumed to be 20 cm.

C. Feasibility Test with Human Subjects Simulating a Claustrophobic Brain or H&N Case A feasibility study of intrafractional head motion management for a claustrophobic patient with H&N cancer was performed to investigate the effectiveness of the system. To be conservative, the simulations were carried out under the assumption that patients were severely claustrophobic, meaning that no immobilization device other than a headrest was provided.

Ten healthy volunteers (age: 30.2±11.2, age range: 20~52) participated in the study and their voluntary head motion reductions with AV-aided interactive guidance were evaluated. Each study consisted of two sessions, one with and the other without guidance to compare the intrafractional head motion. For comparison purposes, the non-interactive session was performed before the AV-aided interactive session. In the sessions without guidance, the system collected motion data while AV-aided interactive guidance was not given to the subject. Each session lasted for five minutes in the TrueBeam treatment room. The AV-aided interactive tablet (unit #1) was placed above the subject's head (using a flexible tablet holder) for AV-aided interactive guidance, and the tracking marker (green colored) was placed on the nose of the subject as shown in FIG. 1. The other tablet (unit #2) was utilized for real-time remote controlling and monitoring (both within and outside the study room) during the session.

The mean displacement was calculated by averaging the absolute values of the displacements (with right-left and superior-inferior data), and the positional drift was calculated by employing a linear fit on the displacements to determine the mm per minute drift. Quantitative statistical comparison of mean right-left and superior-inferior displacements, 95% confidence interval, and positional drift between the two sessions was performed using the paired Student's t-test and evaluated in a spreadsheet program (Excel 2010, Microsoft, Redmond, USA).

Results

A. Basic Characteristics

The mean variation in positional accuracy was 0.3 mm, 0.8 mm and 0.8 mm, and the mean positional resolution was 0.2 mm, 0.3 mm and 0.5 mm with 15 cm, 30 cm and 50 cm of the marker plane-to-camera distance, respectively. The mean variation in temporal accuracy was less than 0.6 ms, and the mean temporal resolution was 24 Hz (42 ms per data point—shown in the screenshot of FIG. 2).

Three angular displacements of 0.28°, 1.43° and 2.86° rotation, in the simulation as provided in the screenshot FIG. 6, caused 1 mm, 5 mm and 10 mm translational motion, respectively. On the image plane, the distances detected by the camera were 0.99 mm, 4.99 mm and 9.98 mm, respectively, resulting in not larger than 0.02 mm error within the range of angular displacement tested.

Figure 7:
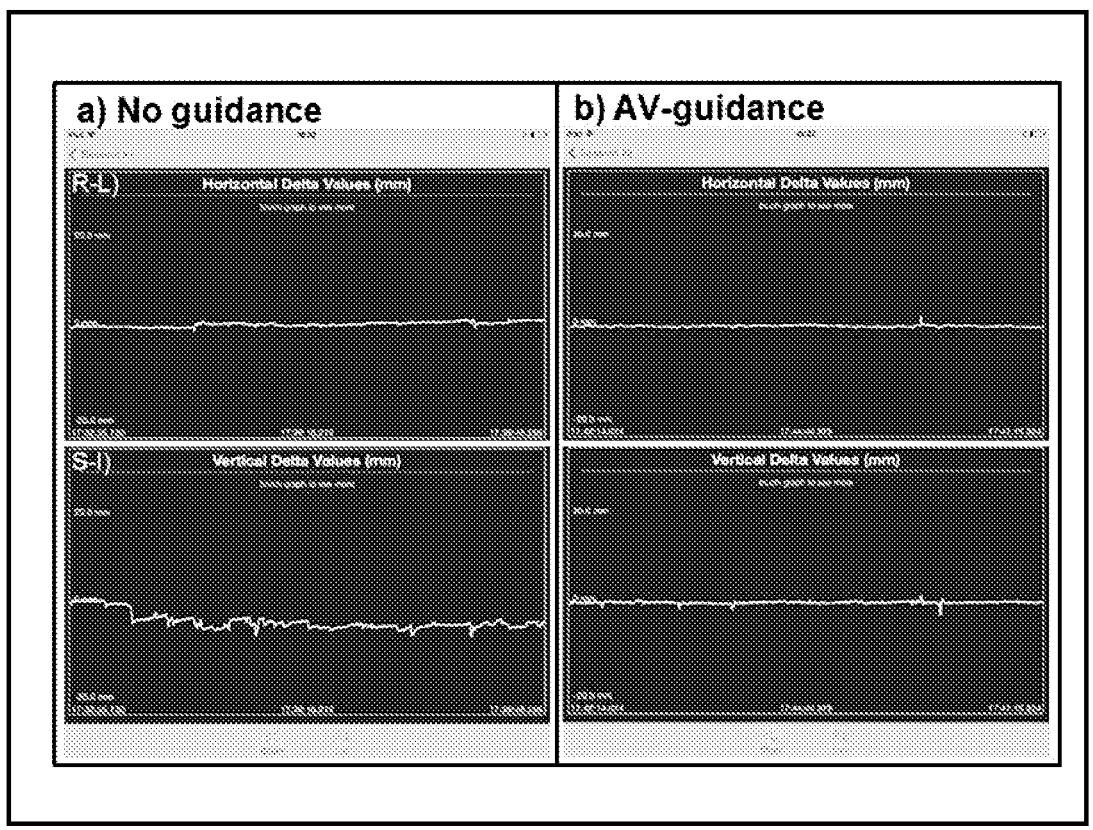
FIGS. 7(A) and (B) provide screenshots of the intrafractional voluntary head motions of the volunteer 8 (representative of the 90th percentile range of reduced the mean displacement due to AV-aided interactive guidance) as shown without AV-aided interactive guidance ("No guidance") and with AV-aided interactive guidance, respectively. The mean displacement decreased superior-inferiorly (SI-direction) by an average of 94% (from 3.5 mm to 0.2 mm) and right-left direction (RL-direction) by an average of 85% (from 0.7 mm to 0.1 mm) with AV-aided interactive guidance.

B. Feasibility Test with Human Subjects Simulating a Claustrophobic Brain or H&N Case In the study, intrafractional voluntary head motion, on average, was kept within 0.4±0.3 mm for the superior-inferior direction with guidance (FIG. 7(B)), showing promising performance while those without guidance (FIG. 7(A)) were 3.2±2.3 mm (p-value=0.002). In addition, intrafractional voluntary head motion in the right-left direction was reduced from 1.3±0.9 mm without guidance (FIG. 7(A)) to 0.2±0.1 mm with guidance (FIG. 7(B)) (p-value=0.01). Compared to the case of no-guidance, the mean displacement was decreased by an average of 89% in the superior-inferior direction and by an average of 82% in the right-left direction.

Noticeable positional drift was also observed in the sessions without AV-aided interactive guidance, while the head position of the volunteers remained almost unchanged with guidance. The average drift was decreased with AV-aided interactive guidance from 0.8±0.6 mm/min to 0.1±0.1 mm/min (87% reduction, p-value=0.004) in the superior-inferior direction and from 0.3±0.2 mm/min to 0.1±0.1 mm/min (66% reduction, p-value=0.01) in the right-left direction.

Referring to Table 1, the table demonstrates means displacement±standard deviation (STD), baseline drift of the right-left and superior-inferior motion, and paired Student t-test p-values with/without AV-aided interactive guidance.

TABLE 1

| Motion direction | | Mean displacement ± STD (mm) | 95% CI | p-value | Baseline drift (mm/min) | p-value |
|---|---|---|---|---|---|---|
| right-left | No guidance | 1.3 ± 0.9 | 0~3.1 | 0.01 | 0.3 ± 0.2 | 0.01 |
| | AV-guidance | 0.2 ± 0.1 (−82%) | 0~0.4 | | 0.1 ± 0.1 (−66%) | |
| superior-inferior | No guidance | 3.2 ± 2.3 | 0~7.8 | <0.001 | 0.8 ± 0.6 | 0.004 |
| | AV-guidance | 0.4 ± 0.3 (−89%) | 0~1.0 | | 0.1 ± 0.1 (−87%) | |

Discussion

In this study, a remote-controlled and self-contained audiovisual-aided interactive system of iPad minis with Retina display was developed for claustrophobic patients with H&N cancer, and its resolution and accuracy, as well as its efficacy when applied to human subjects, were evaluated.

This system provides benefits as a self-contained system of tablet computers. In the study, intrafractional voluntary head motion was reduced from 3.2 mm to 0.4 mm for the superior-inferior direction with guidance, suggesting the reduction of the CTV-PTV margins if the motion is properly managed. Another benefit is that it can be easily accessible by patients, and they could potentially practice AV-aided interactive guidance using their own personal device(s) at the waiting room or even at home. Note that the AV-aided interactive tablet can be used with complete functionality without the remote control tablet. In addition, any iOS device, including iPhone and iPod, can substitute both the AV-aided interactive and remote control components. Due to the widespread commercial availability and use of smart devices, such as iOS devices, the volunteers were already familiar with the devices and had no trouble using them. The system is simple to use and set up, and thus, it can be implemented without difficulty in most clinics, even including places where resources are limited. As mentioned earlier, if the system is installed in waiting areas for patients to practice before they begin radiation therapy treatments or CT simulation, it could improve not only delivery accuracy but also workflow efficiency.

The system utilizes the tablet's built-in front-facing camera to detect motion and consequently is constrained by the inherent resolution and limitations of the camera. The system showed an error range of one pixel, and the corresponding error in millimeters depended on the distance from the camera to the marker. For example, the millimeter-to-pixel ratio was 0.2 mm/pixel at 15 cm and 0.3 mm/pixel at 30 cm. At greater distances, the positional resolution of the system would decrease. In practice, however, it is not likely to have such long distance. As long as the camera is within 50 cm, under 1 mm resolution can be obtained.

A limit of the system may be that the 2D motion tracking method of the current system does not include motion in the third translational dimension (anterior-posterior direction) and rotational errors in the current system. However, the headrest or additional head supports secure the head position in the anterior-posterior direction. In addition, the error resulting from rotational head movements detected by a two-dimensional camera is not significant, if the rotational motion is not huge. For example, as can be observed from FIG. 6, head displacement of around 10 mm caused by a 3 degree rotation would be detected within a relative error of about 0.2% by the system (at 20 cm away from the marker).

In this study, the system tracked a single marker on the subject's open face and detected two translational degrees of freedom. Specifically, the marker was placed on the nose assuming that the nose provides a prominent and relatively fixed area of the face for visual tracking. In a three-dimensional space, three translational planes and three rotational axes exist thus, the two-dimensional motion detection of the system did not reflect true three-dimensional motion. However, the tablet was close in distance to the subject's head, and the subjects were limited in their movements by the physiology of the human head and neck in supine position. Therefore, the present inventors believe, two-dimensional motion detection would be sufficient for intrafractional head motion reduction in the current use case. Although a test is not included in this study, the system can readily track multiple markers on different areas of the face and display the mean displacement of them to obtain better accuracy, if needed. Furthermore, in principle, multi-body-part tracking can be realized using multiple units and markers placed on various body parts. In most head and neck cases, for instance, not only the head but also other relevant body parts, such as shoulders and neck, are important. Therefore, their positions can be identified and corrected during initial image guidance, and a mask on the neck and shoulder can help the patient remain in place. However, if a claustrophobic patient cannot tolerate a mask on the neck and shoulder, additional monitoring may be necessary, and two more iPads can be arranged for real-time monitoring, one for the neck and the other for the shoulders.

In the simulation of the study, the iPad was positioned anterior-inferiorly to the patient's face during treatment to monitor the whole brain motion and to avoid direct irradiation to the iPad. In cases, however, some beam angles with couch kicks in IMRT or VMAT treatments interfere with the current iPad position, and so the iPad can be placed more inferiorly with the aid of visual accessories, such as reflecting glasses.

This embodiment of the system may consist of, for example, two tablets, one for both motion tracing and audiovisual guidance, and the other for remote control. With a router outside the treatment room wired to an access point inside the room, an infrastructure Wi-Fi can be created and both tablets can communicate with each other between the treatment and control rooms. Although it should be appreciated that the router (s) may be located inside, or outside, or a combination thereof. The AV-aided interactive tablet streams frames captured from the front-facing camera to the remote control tablet and can potentially transmit other useful information that can be easily monitored by the remote control tablet. One of this system's benefits is that only a single small mobile device is required in the treatment room for AV-aided interactive guidance, and the remote control device can communicate with the AV-aided interactive tablet anywhere outside of the treatment room.

The iPad close to the beam in the treatment room would be damaged by radiation. To our best knowledge, unfortunately, no systematic study of radiation damage on the iPad has been reported. However, considering that planned replacement of iPad can be easily executed due to both the abundant availability and cost-effectiveness of the device, we believe radiation damage would not be a critical issue.

To bring the proposed system into the clinic, a couple of potential issues need to be considered. First, the proposed 2D monitoring system needs to be verified with an independent system, such as 2D or 3D radiographic imaging. Although the calculations illustrated in FIG. 6 show that head displacement of around 10 mm with a 3 degree head rotation would be detected within a relative error of about 0.2%, verification with an independent imaging system can provide practical guidelines on the use of the proposed system. Second, the audiovisual-aided guidance method used in this study may not be optimal for actual patients, who may have visual or auditory impairments. Therefore, an audiovisual-aided guidance that depends on the visual and auditory capabilities of the specific patient needs to be determined prior to the procedure.

Compared to the most commercially available motion management systems, such as ExacTrac infrared camera system, AlignRT, Real-time Positioning Management (RPM) system (Varian Medical Systems, Palo Alto, USA), and Active Breath Hold (ABC) system (Elekta, Stockholm, Sweden), with limited accessibility by patients, the proposed system is cost-effective so its unique and sufficient functionality of AV-aided interactive guidance in the treatment room as well as in the waiting room can be utilized without substantial financial burden.

Conclusion

This study developed and demonstrated a self-contained AV-aided interactive system for claustrophobic patients with brain or H&N cancer using easily obtainable and cost-effective tablet computers only (iPad mini with Retina display). This approach can potentially streamline clinical flow for claustrophobic patients without a head mask and by allowing patients to practice self-motion management before radiation treatment delivery. To bring the proposed 2D tracking system into the clinic, it needs to be verified with an independent 2D or 3D imaging system.

ADDITIONAL EXAMPLES

Example 1

An aspect of an embodiment of the present invention provides, but not limited thereto, a system for reducing intrafractional motion of a subject The system may comprise a subject user device, whereby the user device may comprise an image acquisition device configured to receive location marker information of the subject to provide location marking data of the subject. The system may comprise: a digital processor configured to: receive the location marking data and determine movement of the subject relative to the location marker information; and communicate feedback of the movement to the subject to help the subject reduce intrafractional motion.

Example 2

The system of example 1, wherein the communication feedback to the subject is in real time.

Example 3

The system of example 1 (as well as subject matter of example 2), wherein the communication feedback of the movement to the subject includes: visual display, audio signal, or both visual and audio.

Example 4

The system of example 3 (as well as subject matter of one or more of any combination of examples 2-3), wherein the visual display is a display panel in communication with the subject user device and which is viewable by the subject.

Example 5

The system of example 4 (as well as subject matter of one or more of any combination of examples 2-3), wherein the digital processor determines a reference point and a movement point, wherein: the reference point represents a starting position of the subject; and the movement point represents an indication of intrafractional motion of the subject.

Example 6

The system of example 4 (as well as subject matter of one or more of any combination of examples 2-3 or 5), wherein display panel includes a display reference point and a display movement point, wherein: the reference point represents to a subject a starting position of the subject; and the display movement point represents to a subject an indication of intrafractional motion of the subject.

Example 7

The system of example 6 (as well as subject matter of one or more of any combination of examples 2-5), wherein: the display reference point is a first color having a preselected pattern, and the display movement point is a second color having a preselected pattern, wherein the intrafractional motion causes the display movement point to move relative to the reference point, and that which is discernable to the subject.

Example 8

The system of example 3 (as well as subject matter of one or more of any combination of examples 2 or 4-7-), wherein the audio signal is provided by a speaker in communication with the subject user device and which is audible by the subject.

Example 9

The system of example 1 (as well as subject matter of one or more of any combination of examples 2-8), further comprising: an operator device, the operator device comprising: an operator digital processor configured to communicate with the subject user device.

Example 10

The system of example 9 (as well as subject matter of one or more of any combination of examples 2-9), wherein the operator digital processor is configured to control and/or monitor the user device.

Example 11

The system of example 9 (as well as subject matter of one or more of any combination of examples 2-8 or 10), wherein the operator device comprises at least one of the following: video display, alpha-numeric input device, or UI navigation device for controlling or monitoring the user device.

Example 12

The system of example 1 (as well as subject matter of one or more of any combination of examples 2-11), wherein the digital processor is configured to control the user device.

Example 13

The system of example 1 (as well as subject matter of one or more of any combination of examples 2-12), wherein the location marker information of the subject is provided by the following: a marking substrate disposed on the subject; a location identified on the subject; or a combination of a marking substrate disposed on the subject and a location identified on the subject.

Example 14

The system of example 1 (as well as subject matter of one or more of any combination of examples 2-13), wherein the determination of movement of the subject is provided by configuring a geometric representation of rotation of the head of the subject.

Example 15

The system of example 14 (as well as subject matter of one or more of any combination of examples 2-13), wherein the geometric representation of rotation of the head of the subject is provided according to the following characteristics:

h, wherein h is the length of the head from the forehead to the back of the head, $\delta$, wherein $\delta$ is the symbol of linear displacement, c, wherein c is the distance from the image acquisition device to a marker at $\delta=0$, $\Delta$, wherein $\Delta$ is the actual linear displacement of the marker caused by the head rotation of $\theta$, $\Phi$, wherein $\Phi$ is the angle of the image acquisition device seeing the displaced marker, d, wherein d is the distance from the image acquisition device to the marker at $\delta=\Delta$, and $\Omega$, wherein $\Omega$ is the calculated displacement by the system.

Example 16

An aspect of an embodiment of the present invention provides, but not limited thereto, a computer implemented method for reducing intrafractional motion of a subject. The method may comprise: receiving location marker information of the subject and generating location marking data of the subject; digitally processing the location marking data and determining movement of the subject relative to the location marker information; and communicating feedback of the movement to the subject to help the subject reduce intrafractional motion.

Example 17

The method of example 16, wherein the communicating the feedback to the subject is performed in real time.

Example 18

The method of example 16 (as well as subject matter of example 17), wherein the communicating the feedback of the movement to the subject includes:

visually displaying the feedback to the subject, audibly signaling the feedback to the subject, or both visually displaying and audibly signaling to the subject.

Example 19

The method of example 16 (as well as subject matter of one or more of any combination of examples 17-18), wherein the digital processing determines a reference point and a movement point, wherein: the reference point represents a starting position of the subject; and the movement point represents an indication of intrafractional motion of the subject.

Example 20

The method of example 19 (as well as subject matter of one or more of any combination of examples 17-19), wherein: the reference point is associated with a first alarm having a preselected audible tone or pitch, and the movement point is associated with a second alarm having a preselected audible tone or pitch, wherein the intrafractional motion causes the second alarm to activate, which is audibly discernable to the subject.

Example 21

The method of example 16 (as well as subject matter of one or more of any combination of examples 17-20), further comprising: operating a controller, wherein operating the controller includes controlling the digital processing and/or the communicating of the feedback.

Example 22

The method of example 21 (as well as subject matter of one or more of any combination of examples 17-20), wherein the operating the controller is performed with at least one of the following: video display, alpha-numeric input device, or UI navigation device.

Example 23

The method of example 16 (as well as subject matter of one or more of any combination of examples 17-22), wherein the location marker information of the subject is provided by the following: providing a marking substrate disposed on the subject; identifying a location on the subject; or a combination of providing a marking a substrate disposed on the subject and identifying a location on the subject.

Example 24

The method of example 16 (as well as subject matter of one or more of any combination of examples 17-23), wherein the determination of movement of the subject is provided by configuring a geometric representation of rotation of the head of the subject.

Example 25

The method of example 24 (as well as subject matter of one or more of any combination of examples 17-23), wherein the geometric representation of rotation of the head of the subject is provided according to the following characteristics:

h, wherein h is the length of the head from the forehead to the back of the head, $\delta$, wherein $\delta$ is the symbol of linear displacement, c, wherein c is the distance from the image acquisition device to a marker at $\delta=0$, $\Delta$, wherein $\Delta$ is the actual linear displacement of the marker caused by the head rotation of $\theta$, $\Phi$, wherein $\Phi$ is the angle of the image acquisition device seeing the displaced marker, d, wherein d is the distance from the image acquisition device to the marker at $\delta=\Delta$, and $\Omega$, wherein $\Omega$ is the calculated displacement by the system.

Example 26

An aspect of an embodiment of the present invention provides, but not limited thereto, a non-transitory machine readable medium including instructions for reducing intrafractional motion of a subject, which when executed by a machine, cause the machine to: receive location marker information of the subject and generate location marking data of the subject; determine movement of the subject relative to the location marker information; and transmit to an output module to communicate feedback of the movement to the subject to help the subject reduce intrafractional motion.

Example 27

The non-transitory medium of claim 26, wherein the output module comprises one or more of the following: memory storage, memory, network, display, or speaker.

Example 28

The non-transitory medium of claim 26, including instructions for reducing intrafractional motion of a subject, which when executed by a machine is capable of performing any one or more of the steps of one or more of Examples 16-25.

Example 29

A method of making or using the system (or portions of the system) as provided in any one or more of Examples 1-14.

REFERENCES

The following patents, applications and publications as listed below and throughout this document are hereby incorporated by reference in their entirety herein (and which are not admitted to be prior art with respect to the present invention by inclusion in this section):

[1] T. Yamamoto, U. Langner, B. W. Loo Jr, J. Shen, P. J. Keall, "Retrospective Analysis of Artifacts in Four-Dimensional CT Images of 50 Abdominal and Thoracic Radiotherapy Patients," International Journal of Radiation Oncology*Biology*Physics 72, 1250-1258 (2008).

[2] S. Kim, Y.-K. Park, J. Lee, K. Choi, S.-J. Ye, "Double-ends quasi-breath-hold (DE-QBH) technique for respiratory motion management," Med Phys 40, 1 (2013).

[3] S. Kim, H. C. Akpati, J. G. Li, C. R. Liu, R. J. Amdur, J. R. Palta, "An immobilization system for claustrophobic patients in head-and-neck intensity-modulated radiation therapy," International Journal of Radiation Oncology*Biology*Physics 59, 1531-1539 (2004).

[4] G. C. Bentel, L. B. Marks, K. Hendren, D. M. Brizel, "Comparison of two head and neck immobilization systems," International Journal of Radiation Oncology*Biology*Physics 38, 867-873 (1997).

[5] P. Keall, G. Mageras, J. Balter, R. Emery, K. Forster, S. Jiang, J. Kapatoes, D. Low, M. Murphy, B. Murray, C. Ramsey, M. Van Herk, S. Vedam, J. Wong, E. Yorke, "The management of respiratory motion in radiation oncology report of AAPM Task Group 76," Med Phys 33, 3874-3900 (2006).

[6] R. B. Venkat, A. Sawant, Y. Suh, R. George, P. J. Keall, "Development and preliminary evaluation of a prototype audiovisual biofeedback device incorporating a patient-specific guiding waveform," Physics in medicine and biology 53, N197 (2008).

[7] S. Kim, R. D. Helmig, "Interactive patient immobilization system," (Google Patents, 2010).

[8] S. K. Kim, H. Chung, H. Jin, J. Palta, T.-S. Suh, R. Helmig, "Laser-Guided Interactive Patient Immobilization System for the Brain or Head and Neck Treatment" Medical physics; ICMP (14th), 838-839 (2005).

[9] R. George, T. D. Chung, S. S. Vedam, V. Ramakrishnan, R. Mohan, E. Weiss, P. J. Keall, "Audio-visual biofeedback for respiratory-gated radiotherapy: Impact of audio instruction and audio-visual biofeedback on respiratory-gated radiotherapy," Int J Radiat Oncol Biol Phys 65, 924-933 (2006).

[10] T. Kim, S. Pollock, D. Lee, R. O'Brien, P. Keall, "Audio-visual biofeedback improves diaphragm motion reproducibility in MRI," Medical Physics 39, 6921 (2012).

[11] S. Lim, S. H. Park, S. D. Ahn, Y. Suh, S. S. Shin, S.-w. Lee, J. H. Kim, E. K. Choi, B. Y. Yi, S. I. Kwon, S. Kim, T. S. Jeung, "Guiding curve based on the normal breathing as monitored by thermocouple for regular breathing," Medical Physics 34, 4514-4518 (2007).

[12] J. F. T. Arnold, P. Mörchel, E. Glaser, E. D. Pracht, P. M. Jakob, "Lung MRI using an MR-compatible active breathing control (MR-ABC)," Magnetic Resonance in Medicine 58, 1092-1098 (2007).

[13] T. Kim, R. Pooley, D. Lee, P. Keall, R. Lee, S. Kim, "Quasi-breath-hold (QBH) Biofeedback in Gated 3D Thoracic MRI: Feasibility Study," Progress in Medical Physics 25, 72-78 (2014).

[14] Y. K. Park, S. Kim, H. Kim, I. I. H. Kim, K. Lee, S. J. Ye, "Quasi-breath-hold technique using personalized audio-visual biofeedback for respiratory motion management in radiotherapy," Medical Physics 38, 3114 (2011).

[15] S. J. McKenna, Y. Raja, S. Gong, "Tracking colour objects using adaptive mixture models," Image and vision computing 17, 225-231 (1999).

The devices, systems, non-transitory computer readable medium, components, modules, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

A. Kim, S., et al., "An Immobilization System for Claustrophobic Patients in Head-and-Neck Intensity-Modulated Radiation Therapy", Int. J. Radiation Oncology Biol. Phys., Vol. 59, No. 5, pp. 1531-1539, 2004.

B. Li, G., et al., "Migration from full-head mask to "open-face" mask for immobilization of patients with head and neck cancer", Journal of Applied Clinical Medical Physics, Vol. 14, No. 5, 2013, pp 243-254.

C. U.S. Patent Application Publication No. US 2007/0093723 A1, Keall, et al., "Method and Apparatus for Respiratory Audio-Visual Biofeedback for Imaging and Radiotherapy", Apr. 26, 2007.

D. International Patent Application Serial No. WO 2014/116868 A1, Yu, et al., "Systems, Devices, and Methods for Tracking and Compensating for Patient Motion During a Medical Imaging Scan", Jul. 31, 2014.

E. U.S. Patent Application Publication No. US 2013/0289796 A1, Bergfjord, et al., "Vision System for Radiotherapy Machine Operator", Oct. 31, 2013.

F. International Patent Application Publication No. WO 2012/033739 A2, Karahalios, et al., "Surgical and Medical Instrument Tracking Using a Depth-Sensing Device", Mar. 15, 2012.

G. U.S. Pat. No. 8,754,805 B2, Wang, et al., "Method and Apparatus for Image-Based Positioning", Jun. 17, 2014.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A system for reducing intrafractional motion of a subject, the system comprising:
a subject user device, said user device comprising:
an image acquisition device configured to receive location marker information of the subject to provide location marking data of the subject;
a digital processor configured to:
receive said location marking data and determine movement of the subject relative to the location marker information, wherein said determination of movement of the subject is provided by configuring a geometric representation of rotation of the head of the subject, wherein said geometric representation of rotation of the head of the subject is provided according to the following characteristics:
h, wherein h is the length of the head from the forehead to the back of the head,
δ, wherein δ is the symbol of linear displacement,
c, wherein c is the distance from said image acquisition device to a marker at δ=0,
Δ, wherein Δ is the actual linear displacement of said marker caused by the head rotation of θ,
Φ, wherein Φ is the angle of said image acquisition device seeing the displaced marker,
d, wherein d is the distance from said image acquisition device to the marker at δ=Δ, and
Ω, wherein Ω is the calculated displacement by the system; and
communicate feedback of the movement to the subject to help the subject reduce intrafractional motion.

2. The system of claim 1, wherein said communication feedback to the subject is in real time.

3. The system of claim 1, wherein said communication feedback of the movement to the subject includes:
visual display,
audio signal, or
both visual and audio.

4. The system of claim 3, wherein said visual display is a display panel in communication with said subject user device and which is viewable by the subject.

5. The system of claim 4, wherein said digital processor determines a reference point and a movement point, wherein:
said reference point represents a starting position of the subject; and
said movement point represents an indication of intrafractional motion of the subject.

6. The system of claim 4, wherein display panel includes a display reference point and a display movement point, wherein:
said reference point represents to a subject a starting position of the subject; and
said display movement point represents to a subject an indication of intrafractional motion of the subject.

7. The system of claim 6, wherein:
said display reference point is a first color having a preselected pattern, and
said display movement point is a second color having a preselected pattern, wherein the intrafractional motion causes the display movement point to move relative to the reference point, and that which is discernable to the subject.

8. The system of claim 3, wherein said audio signal is provided by a speaker in communication with said subject user device and which is audible by the subject.

9. The system of claim 1, further comprising:
an operator device, said operator device comprising:
an operator digital processor configured to communicate with said subject user device.

10. The system of claim 9, wherein said operator digital processor is configured to control and/or monitor said user device.

11. The system of claim 9, wherein said operator device comprises at least one of the following: video display, alpha-numeric input device, or UI navigation device for controlling or monitoring said user device.

12. The system of claim 1, wherein said digital processor is configured to control said user device.

13. The system of claim 1, wherein said location marker information of the subject is provided by the following:
a marking substrate disposed on the subject;
a location identified on the subject; or
a combination of a marking substrate disposed on the subject and a location identified on the subject.

14. A computer implemented method for reducing intrafractional motion of a subject, the method comprising:
receiving location marker information of the subject and generating location marking data of the subject;
digitally processing said location marking data and determining movement of the subject relative to the location marker information, wherein said determination of movement of the subject is provided by configuring a geometric representation of rotation of the head of the subject, wherein said geometric representation of rotation of the head of the subject is provided according to the following characteristics:
h, wherein h is the length of the head from the forehead to the back of the head,
δ, wherein δ is the symbol of linear displacement,
c, wherein c is the distance from said image acquisition device to a marker at δ=0,
Δ, wherein Δ is the actual linear displacement of said marker caused by the head rotation of θ,
Φ, wherein Φ is the angle of said image acquisition device seeing the displaced marker,
d, wherein d is the distance from said image acquisition device to the marker at δ=Δ, and
Ω, wherein Ω is the calculated displacement by the system; and
communicating feedback of the movement to the subject to help the subject reduce intrafractional motion.

15. The method of claim 14, wherein said communicating the feedback to the subject is performed in real time.

16. The method of claim 14, wherein said communicating the feedback of the movement to the subject includes:
visually displaying said feedback to the subject,
audibly signaling said feedback to the subject, or
both visually displaying and audibly signaling to the subject.

17. The method of claim 14, wherein said digital processing determines a reference point and a movement point, wherein:

said reference point represents a starting position of the subject; and said movement point represents an indication of intrafractional motion of the subject.

18. The method of claim 17, wherein:
said reference point is associated with a first alarm having a preselected audible tone or pitch, and
said movement point is associated with a second alarm having a preselected audible tone or pitch, wherein the intrafractional motion causes the second alarm to activate, which is audibly discernable to the subject.

19. The method of claim 14, further comprising:
operating a controller, wherein operating the controller includes controlling said digital processing and/or said communicating of the feedback.

20. The method of claim 19, wherein said operating the controller is performed with at least one of the following: video display, alpha-numeric input device, or UI navigation device.

21. The method of claim 14, wherein said location marker information of the subject is provided by the following:
providing a marking substrate disposed on the subject;
identifying a location on the subject; or
a combination of providing a marking a substrate disposed on the subject and identifying a location on the subject.

22. A non-transitory machine readable medium including instructions for reducing intrafractional motion of a subject, which when executed by a machine, cause the machine to:
receive location marker information of the subject and generate location marking data of the subject;
determine movement of the subject relative to the location marker information, wherein said determination of movement of the subject is provided by configuring a geometric representation of rotation of the head of the subject, wherein said geometric representation of rotation of the head of the subject is provided according to the following characteristics:
h, wherein h is the length of the head from the forehead to the back of the head,
$\delta$, wherein $\delta$ is the symbol of linear displacement,
c, wherein c is the distance from said image acquisition device to a marker at $\delta=0$,
$\Delta$, wherein $\Delta$ is the actual linear displacement of said marker caused by the head rotation of $\theta$,
$\Phi$, wherein $\Phi$ is the angle of said image acquisition device seeing the displaced marker,
d, wherein d is the distance from said image acquisition device to the marker at $\delta=\Delta$, and
$\Omega$, wherein $\Omega$ is the calculated displacement by the system; and
transmit to an output module to communicate feedback of the movement to the subject to help the subject reduce intrafractional motion.

23. The non-transitory machine readable medium of clam 22, wherein said output module comprises one or more of the following: memory storage, memory, network, display, or speaker.

24. The non-transitory machine readable medium of clam 22, wherein said communication feedback to the subject is in real time.

25. The non-transitory machine readable medium of claim 22, wherein when executed by the machine, causes the machine to determine a reference point and a movement point, wherein:
said reference point represents a starting position of the subject; and
said movement point represents an indication of intrafractional motion of the subject.

* * * * *